US010292950B2

(12) United States Patent
McKearn et al.

(10) Patent No.: US 10,292,950 B2
(45) Date of Patent: *May 21, 2019

(54) METHOD OF TREATMENT WITH ANTI-INFLAMMATORY AND ANALGESIC COMPOUNDS WHICH ARE GI-, RENAL-, AND PLATELET-SPARING

(71) Applicant: Pathologica LLC, San Francisco, CA (US)

(72) Inventors: John McKearn, St. Louis, MO (US); Jeremy Blitzer, San Francisco, CA (US)

(73) Assignee: Pathologica LLC, San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/594,199

(22) Filed: May 12, 2017

(65) Prior Publication Data

US 2018/0369170 A1    Dec. 27, 2018

Related U.S. Application Data

(60) Division of application No. 14/033,738, filed on Sep. 23, 2013, now Pat. No. 9,675,566, which is a continuation-in-part of application No. 13/556,948, filed on Jul. 24, 2012, now Pat. No. 8,609,734, which is a continuation of application No. 12/837,753, filed on Jul. 16, 2010, now Pat. No. 8,258,186.

(60) Provisional application No. 62/290,095, filed on Dec. 24, 2009, provisional application No. 62/226,060, filed on Jul. 16, 2009, provisional application No. 61/704,104, filed on Sep. 21, 2012.

(51) Int. Cl.
| | |
|---|---|
| A61K 9/48 | (2006.01) |
| A61K 31/13 | (2006.01) |
| A61K 31/15 | (2006.01) |
| A61P 29/00 | (2006.01) |
| A61K 31/155 | (2006.01) |

(52) U.S. Cl.
CPC .......... *A61K 31/155* (2013.01); *A61K 9/4858* (2013.01); *A61K 9/4866* (2013.01); *A61K 9/4891* (2013.01); *A61K 31/13* (2013.01); *A61K 31/15* (2013.01); *A61P 29/00* (2018.01)

(58) Field of Classification Search
CPC ................................ A61K 31/15; A61P 29/00
USPC ........................................... 514/632; 424/450
See application file for complete search history.

(56) References Cited

U.S. PATENT DOCUMENTS

| | | | |
|---|---|---|---|
| 4,201,788 A | 5/1980 | Voorhees | |
| 4,520,031 A | 5/1985 | Knight, III | |
| 5,580,715 A | 12/1996 | McGrath | |
| 5,614,557 A | 3/1997 | Bey | |
| 5,639,600 A | 6/1997 | McGrath | |
| 5,744,122 A | 4/1998 | McGrath | |
| 6,537,523 B1 | 3/2003 | McGrath | |
| 6,544,541 B1 | 4/2003 | Zahradka | |
| 6,924,095 B2 | 8/2005 | McGrath | |
| 7,087,648 B1 | 8/2006 | McGrath | |
| 7,198,946 B2 | 4/2007 | Marton | |
| 7,445,794 B1 | 11/2008 | Newell | |
| 7,754,765 B2 | 7/2010 | Wang | |
| 7,879,914 B2 | 2/2011 | McGrath et al. | |
| 8,258,186 B2 * | 9/2012 | McKearn ............. | A61K 9/2018 514/632 |
| 8,445,540 B2 | 5/2013 | Hadlock et al. | |
| 8,609,734 B2 * | 12/2013 | McKearn ............. | A61K 9/2018 514/632 |
| 8,858,991 B2 * | 10/2014 | McKearn ............. | A61K 9/2054 424/451 |
| 9,668,988 B2 | 6/2017 | McKearn | |
| 9,675,566 B2 * | 6/2017 | McKearn ............. | A61K 9/4891 |
| 9,867,794 B2 | 1/2018 | Hadlock | |
| 2003/0130357 A1 | 7/2003 | Ramesh | |
| 2003/0175832 A1 | 9/2003 | Marton | |
| 2004/0219208 A1 | 11/2004 | Kawamura | |
| 2005/0042277 A1 | 2/2005 | Srinivas | |
| 2005/0159493 A1 | 7/2005 | McGrath | |
| 2005/0256207 A1 | 11/2005 | McGrath | |
| 2006/0160087 A1 | 7/2006 | McGrath | |
| 2007/0078187 A1 | 4/2007 | McGrath | |
| 2008/0262092 A1 | 10/2008 | Hadlock | |
| 2009/0017114 A1 | 1/2009 | Heasley | |
| 2009/0181089 A1 | 7/2009 | Schellekens | |
| 2010/0189790 A1 | 7/2010 | Safadi | |
| 2011/0091418 A1 | 4/2011 | McGrath | |
| 2011/0112199 A1 | 5/2011 | McKearn | |
| 2012/0219970 A1 | 8/2012 | McGrath | |
| 2012/0269891 A1 | 10/2012 | McKearn | |
| 2012/0289604 A1 | 11/2012 | McKearn | |
| 2013/0317113 A1 | 11/2013 | Hadlock | |
| 2014/0051765 A1 | 2/2014 | McKearn | |
| 2014/0187643 A1 | 7/2014 | McKearn | |

(Continued)

FOREIGN PATENT DOCUMENTS

| | | |
|---|---|---|
| CN | 101300004 A | 11/2008 |
| EP | 1389480 A1 | 2/2004 |

(Continued)

OTHER PUBLICATIONS

"2343075", Wikipedia, Available from the Internet, <URL: https://en.wikipedia.org/w/index.php?title=Fingolimod&oldid=524066559>, Last Retrieved Oct. 12, 2017, Published Nov. 20, 2012 according to Wikipedia.

(Continued)

*Primary Examiner* — Kevin E Weddington
(74) *Attorney, Agent, or Firm* — Dennis A. Bennett; Cynthia Hathaway; Clifford A. Schlecht

(57) ABSTRACT

Disclosed herein are compounds, pharmaceutical compositions, and methods for the treatment of diseases such as inflammation and/or pain, comprising the administration of a therapeutically effective amount of a non-steroidal, non-opioid compound having GI-/renal-/platelet-sparing activities, and wide safety margins with no appreciable inhibition of either form of cyclooxygenase.

18 Claims, 2 Drawing Sheets

(56) References Cited

U.S. PATENT DOCUMENTS

| | | |
|---|---|---|
| 2014/0377345 A1 | 12/2014 | McKearn |
| 2015/0359761 A1 | 12/2015 | Blitzer |
| 2017/0290788 A1 | 10/2017 | McKearn |
| 2018/0050000 A1 | 2/2018 | McKearn |
| 2018/0360783 A1 | 12/2018 | Blitzer |

FOREIGN PATENT DOCUMENTS

| | | |
|---|---|---|
| EP | 2283830 A1 | 2/2011 |
| EP | 2343075 A1 | 7/2011 |
| WO | 1996021450 A2 | 7/1996 |
| WO | 1999021542 A2 | 5/1999 |
| WO | 2000074742 A1 | 12/2000 |
| WO | 0160392 A1 | 8/2001 |
| WO | 03089601 A2 | 10/2003 |
| WO | 2004089341 A1 | 10/2004 |
| WO | 2005041988 A1 | 5/2005 |
| WO | 2006081431 | 8/2006 |
| WO | 2006091522 A2 | 8/2006 |
| WO | 2007016338 A2 | 2/2007 |
| WO | 2007035957 A2 | 3/2007 |
| WO | 2008112656 | 9/2008 |
| WO | 2008112659 | 9/2008 |
| WO | 2009018368 | 2/2009 |
| WO | 2010037395 A2 | 4/2010 |
| WO | 2010045265 A1 | 4/2010 |
| WO | 2010066203 A1 | 6/2010 |
| WO | 2011009039 A2 | 1/2011 |
| WO | 2011080344 | 7/2011 |
| WO | 2012100043 A2 | 7/2012 |
| WO | 2014110154 A1 | 7/2014 |

OTHER PUBLICATIONS

Ackerman, J. et al., Drugs Affecting the Cell Cycle via Actions on the Polyamine Metabolic Pathway, Progress in Cell Cycle Res. 5, 461-468, 2003.

Allan et al., Role of the Integrin-Binding Protein Osteopontin in Lymphatic Metastasis of Breast Cancer, Am J Pathol. 169(1), 233-246, 2006.

Ang, C. et al., Plasma Osteopontin Levels are Predictive of Disease Stage in Patients With Transitional Cell Carcinoma of the Bladder, BJU Int. 96, 803-805, 2005.

Banerjee, S. et al., Gene Expression Profiling in Inflammatory Airway Disease Associated With Elevated Adenosine, Am J Physiol Lung Cell Mol Physiol. 282, 169-182, 2002.

Bao, L. et al., Osteopontin in Metastatic Lesions as a Prognostic Marker in Ovarian Cancers, J Biomed Sci. 14, 373-381, 2007.

Birnbaum, G., Long-Term Disease-Modifying Therapies, Multiple Sclerosis, Ch. 8, Feb. 1-18, 2009.

Bitonti et al., Characterization of Trypanosoma brucei brucei S-adenosyl-L-methionine decarboxylase and its inhibition by Berenil, pentamidine and methylglyoxal bis(guanylhydrazone). Biochem J. 237(3): 685-9 (1986).

Boeshore, K. et al., Novel Changes in Gene Expression Following Axotomy of a Sympathetic Ganglion: A Microarray Analysis, J Neurobiol. 59, 216-235, 2004.

Bonvini, JM et al., Lack of In Vivo Function of Osteopontin in Experimental Anti-GBM Nephritis, J Am Soc Nephrol. 11, 1647-1655, 2000.

Bramwell et al., Serial plasma osteopontin levels have prognostic value in metastatic breast cancer. Clin Cancer Res. 12(11 Pt 1):3337-43 (2006).

Brown, L. et al., Osteopontin Expression and Distribution in Human Carcinomas, Am J Pathol 145(3), 610-623,1994.

Bruemmer, D. et al., Angiotensin II-Accelerated Atherosclerosis and Aneurysm Formation is Attenuated in Osteopontin-Deficient Mice, J Clin Invest. 112(9), 1318-1331, 2003.

Chabas D et al., 'The Infuence of the Proinfammatory Cytokine, Osteopontin, on Autoimmune Demyelinating Disease,' Science, Nov. 23, 2001, 294(5547): 1731-5.

Chambers, A. et al., Osteopontin Expression in Lung Cancer, Lung Cancer 15, 311-323, 1996.

Chiocchetti, A. et al., High Levels of Osteopontin Associated with Polymorphisms in its Gene are a Risk Factor for Development of Autoimmunity/Lymphoproliferation, Blood 103(4), 1376-1382, 2004.

Coppola D et al., Correlation of osteopontin protein expression and pathological stage across a wide variety of tumor histologies. Clin Cancer Res. 10(1 Pt 1):184-90 (2004).

Cronstein, B., Low-Dose Methotrexate: A Mainstay in the Treatment of Rheumatoid Arthritis, Pharm Revs. 57(2), 163-172, 2005.

Della Ragione, F. et al., Effect of Analogues of 5'-Methylthioadenosine on Cellular Metabolism, Biochem J. 210, 429-435, 1983.

Denhardt, D. et al., Role of Osteopontin in Cellular Signaling and Toxicant Injury, Annu Rev Pharmacol Toxicol. 41, 723-749, 2001.

Dunzendorfer, U., Some aspects of clearance of mitoguazone in cancer patients and experimental cancer models, Arzneimittel-Forschung (1986), 36(3), 506-8 CODEN: ARZNAD; ISSN: 0004-4172.

Ekelund, S. et al., Guanidino-Containing Drugs in Cancer Chemotherapy: Biochemical and Clinical Pharmacology, Biochem Pharmacol. 61, 1183-1193, 2001.

EP 2121586 Extended European Search Report, dated Jul. 22, 2011, 27 pages.

EP 2453886 Extended European Search Report, dated Nov. 5, 2012, 7 pages.

Fedarko, N. et al., Elevated Serum Bone Sialoprotein and Osteopontin in Colon, Breast, Prostate, and Lung Cancer, Clin Cancer Res. 7, 4060-4066, 2001.

Fischer D et al., A role for adenosine deaminase in human monocyte maturation, J Clin Invest. 58(2):399-407 (1976).

Freedlander, B.L., Carcinostatic Action of Polycarbonyl Compounds and Their Derivatives II. Glyoxal Bis (Guanylhydrazone) and Derivatives, Cancer Res. (1958) vol. 18, Apr. (No. 4): 360-63.

Freedlander, B.L., Carcinostatic Action of Polycarbonyl Compounds and Their Derivatives III. Hydroxymethylglyoxal Bis(guanylhydrazone), Cancer Res. (1958) vol. 18 Dec. (No. 12): 1286-89.

Freireich, E. et al., Methylglyoxal Bis (Guanylhydrazone): A New Agent Active Against Acute Myelocytic Leukemia, Cancer Chemotherapy Reports 16, 183-186, 1962.

Furger, K. et al., The Functional and Clinical Roles of Osteopontin in Cancer and Metastasis, Curr Mol Med. 1(5), 321-632, 2001.

Giannessi F, 'Carnitine Palmitoyltransferase Inhibitors in the Management of Type 2 Diabetes: An Old Promise to Be Maintained,' Drugs of the Future, Prous Science, ES, (Apr. 1, 2003), vol. 28, No. 4, doi:DOI:10.1358/DOF.2003.028.04.725499, ISSN 0377-8282, pp. 371-381, XP009047902.

Guo X et al., 'Spermidine alleviates severity of murine experimental autoimmune encephalomyelitis,' Invest Ophthalmol Vis Sci, Apr. 1, 2011, 52(5): 2696-703.

Hadjimichael, O. et al., Persistent Pain and Uncomfortable Sensations in Persons With Multiple Sclerosis, Pain 127, 35-41, 2007.

Harth, M. et al., Monocyte Dependent Excited Oxygen Radical Generation in Rheumatoid Arthritis: Inhibition by Gold Sodium Thiomalate, J Rheumatol 10(5), 701-707, 1983.

Hasko G et al., Shaping of monocyte and macrophage function by adenosine receptors. Pharmacol Ther. 113 (2):264-75 (2007, e-published Sep. 2006).

Herr, H. et al., Phase 1 Trial of Alpha-Difluoromethyl Ornithine (DFMO) and Methylglyoxal Bis (Guanylhydrazone) MGBG) in Patients With Advanced Prostatic Cancer, Urology 28(6), 508-511, 1986.

Hershfield, M., New Insights Into Adenosine-Receptor-Mediated Immunosuppression and the Role of Adenosine in Causing the Immunodeficiency Associated With Adenosine Deaminase Deficiency, Eur J Immunol. 35, 25-30, 2005.

Hibasami, H. et al., Studies of Inhibition of Rat Spermidine Synthase and Spermine Synthase, Biochem J. 187, 419-428, 1980.

Huang, Y. et al., Molecular Mechanisms of Polyamine Analogs in Cancer Cells, Anti-Cancer Drugs 16, 229-241, 2005.

Hur, EM et al., Osteopontin-Induced Relapse and Progression of Autoimmune Brain Disease Through Enhanced Survival of Activated T Cells, Nature Immunol. 8(1), 74-83, 2007.

(56) References Cited

OTHER PUBLICATIONS

Jensen, B., Dialyzability of Methyl Glyoxal Bis Guanyl Hydrazone, Cancer Treatment Reports, (1983) vol. 67, No. 3, pp. 283-284. CODEN: CTRRDO. ISSN: 0361-5960.
Kaczmarek L et al., Inhibitors of polyamine biosynthesis block tumor necrosis factor-induced activation of macrophages. Cancer Res 52:1891-4 (1992).
Kamatani N et al., Dependence of adenine production upon polyamine synthesis in cultured human lymphoblasts. Biochim Biophys Acta. 675(3-4):344-50 (1981).
Kaminska et al., Pretreatment serum levels of cytokines and cytokine receptors in patients with non-small cell lung cancer, and correlations with clinicopathological features and prognosis. M-CSF—an independent prognostic factor. Oncology. 70(2):115-25 (2006).
Kawamura, K. et al., Differentiation, Maturation, and Survival of Dendritic Cells by Osteopontin Regulation, Clin Diagn Lab Immunol. 12(1), 206-212, 2005.
Kelsen, D. et al., Phase II Trials of Methylglyoxal-bis (Guanylhydrazone), Am J Clin Oncol 5, 221-225, 1982.
Khan, G., "Controlled Release Oral Dosage Forms: Some Recent Advances in Matrix Type Drug Delivery Systems," The Sciences 1(5), 350-354, 2001.
Kim JH et al., Osteopontin as a potential diagnostic biomarker for ovarian cancer. JAMA. 287(13):1671-9 (2002).
Knight, W.A. III et al., "Phase I-II trial of methyl-GAG: a Southwest Oncology Group Pilot Study," Cancer Treat Rep. 63 (11-12):1933-7 (1979).
Levin, Robert H., Different patterns of remission in acute myelocytic leukemia. A comparison of the effects of the methylglyoxal bis(guanylhydrazone) and 6-mercaptopurine, Blood (1963), 21, 689-98 CODEN: BLOOAW; ISSN: 0006-4971.
Liaw L et al., Altered wound healing in mice lacking a functional osteopontin gene (spp1). J Clin Invest. 101(7):1468-78 (1998).
Lieber, C. et al., S-Adenosylmethionine: Molecular, Biological, and Clinical Aspects—An Introduction, Am J Clin Nutr 76(suppl), 1148S-1150S, 2002.
Liesmann, J. etal., Pharmacokinetics of Methyl-Gloxyl Bis-Guanylhydrozone (MGBG), AACR Abstracts 605, 151, 1980.
Lim S W et al: 'MGBG Therapy of Relapsed Extralymphatic, i HIV-Associated Non-Hodgkin's Lymphoma (HIV NHL)', Proceedings. American Society of Clinical Oncology, Meeting, Waverly Press, Baltimore, MD, US, vol. 14, Mar. 1, 1995 (Mar. 1, 1995), p. A1274.
Maddox, A.M., Polyamines increase in human peripheral blood and bone marrow mononuclear cells following administration of methylglyoxal bis(guanylhydrazone), Chemotherapy, (1988) vol. 34, No. 5, pp. 419-429. Journal code: 0144731. ISSN: 0009-3157.
Manni et al., 'Cellular mechanisms mediating the anti-invasive properties of the ornithine decarboxylase inhibitor [alpha]-difluoromethylornithine (DFMO) in human breast cancer cells', Clinical & Experimental Metastasis ; Official Journal of the Metastasis Research Society, Kluwer Academic Publishers, DO, (Dec. 1, 2004), vol. 21, No. 5, doi:DOI:10.1007/S10585-004-2724-3, ISSN 1573-7276, pp. 461-467, XP019235769.
Marton, et al., 'Polyamines as Targets for Therapeutic Intervention.' Ann. Rev. Pharm. Toxicol., vol. 35, 55-91, (1995).
Matsui, Y. et al., Osteopontin Deficiency Attenuates Atherosclerosis in Female Apolipoprotein E-Deficient Mice, Arterioscler Thromb Vase Biol. 23, 1029-1034, 2003.
Maubec et al., 'Subcutaneous Inflammatory Edema Induced by MINE Chemotherapy', Annales de dermatologie et de venerologie, vol. 128, No. 4, pp. 534-537 (Apr. 2001). See enclosed translated abstract.
Mazzali, M. etal., Osteopontin—A Molecule for All Seasons, QJM 95, 3-13, 2002.
Messina, L. et al., Polyamine Involvement in Functional Activation of Human Macrophages, J Leukoc Biol. 52, 585-587, 1992.
Mezzano et al., Overexpression of chemokines, fibrogenic cytokines, and myofibroblasts in human membranous nephropathy. Kidney Int. 57(1):147-58 (2000).

Mi, Zhiyong et al., Differential osteopontin expression in phenotypically distinct subclones of murine breast cancer cells mediates metastatic behavior. J Biol Chem. 279(45): 46659-67 (2004).
Mihich, E. et al., Pharmacology of Methylglyoxal-bis-(guanylhydrazone) (CH3-G) I. Toxic and Pathologic Effects, Cancer Res, (1962) vol. 22, Sep. (No. 9) pp. 962-972 (plus figs).
Mihich, E., Anti-Tumor Effects and Toxicology of Methylglyoxal Bis (Guanylhydrazone), Proc. Nat. Acad. Sciences Abstracts 1959.
Mihich, Enrico, Current Studies with Methylglyoxal-bis(guanylhydrazone), Cancer Res, (1963) vol. 23, Sep. (No. 9) pp. 1375-1389.
Mitoguazone, "Drugs of the Future," 1992 ES, (1992), vol. 17, No. 3, ISSN 0377-8282, pp. 253-254, XP009190054.
Mor G et al., Serum protein markers for early detection of ovarian cancer. Proc Natl Acad Sci USA. 102(21):7677-82 (2005).
Nemir, M. et al., Targeted Inhibition of Osteopontin Expression in the Mammary Gland Causes Abnormal Morphogenesis and Lactation Deficiency, J Biol Chem. 275(2), 969-976, 2000.
Noiri E, et al. Reduced tolerance to acute renal ischemia in mice with a targeted disruption of the osteopontin gene. Kidney Int. 56(1):74-82 (1999).
NZ 597488 Examination Report, dated Aug. 8, 2012, 2 pages.
Oates et al., The identification of osteopontin as a metastasis-related gene product in a rodent mammary tumour model. Oncogene. 13(1):97-104 (1996).
Ohmori R et al., Plasma osteopontin levels are associated with the presence and extent of coronary artery disease. Atherosclerosis. 170(2):333-7 (2003).
Okada H et al., Tubular osteopontin expression in human glomerulonephritis and renal vasculitis. Am J Kidney Dis. 36 (3):498-506 (2000).
Oliverio, V. et al., The Distribution, Excretion, and Metabolism of Methylglyoxal-Bis-Guanylhydrazone-C14, Clin Pharmacol and Experimental Thera Ser. 141, 149-156, 1963.
Panzer U et al., Monocyte chemoattractant protein-1 and osteopontin differentially regulate monocytes recruitment in experimental glomerulonephritis. Kidney Int. 59(5):1762-9 (2001).
Pelleteir, D. et al., "Fingolimod for Multiple Sclerosis," New Eng. J. Med. 2012 vol. 366 pp. 339-347.
Pixley et al., CSF-1 regulation of the wandering macrophage: complexity in action. Trends Cell Biol. 14(11):628-38 (2004).
Pixley, F. et al., Protein Tyrosine Phosphatase Phi Regulates Paxillin Tyrosine Phosphorylation and Mediates Colony-Stimulating Factor 1-Induced Morphological Changes in Macrophages, Mol Cell Biol. 21(5), 1795-1809, 2001.
Regelson, William, Clinical experience with methylglyoxal bis(guanylhydrazone) dihydrochloride: A new agent with clinical activity in acute myelocytic leukemia and the lymphomas., Cancer Chemother Repts, (1963) vol. 27, pp. 15-26.
Regelson, William, Initial clinical study of parenteral methylglyoxal bis(guanylhydrazone) diacetate, Cancer Chemother Repts, (1961) vol. 11, pp. 81-86.
Regenass U et al., CGP 48664, A new S-adenosylmethionine decarboxylase inhibitor with broad spectrum antiproliferative and antitumor activity. Cancer Res. 54(12): 3210-3217 (1994).
Renkl et al., Osteopontin functionally activates dendritic cells and induces their differentiation toward a Th1-polarizing phenotype. Blood. 106(3):946-55 (2005).
Rittling SR et al., Osteopontin function in pathology: lessons from osteopontin-deficient mice. Exp Nephrol. 7(2):103-13 (1999).
Roach, H., "Arthritis & Rheumatism," 2008, Journal of the American College of Rheumatology, 58(8), pp. 2217-2218.
Rudland et al., Prognostic significance of the metastasis-associated protein osteopontin in human breast cancer. Cancer Res. 62(12):3417-27 (2002).
Sakaguchi H et al., Clinical implications of osteopontin in metastatic lesions of uterine cervical cancers. Cancer Lett. 247(1):98-102 (2007).
Salvi, M. et al., The Effect of Methylglyoxal-Bis (Guanylhydrazone) on Mitochondrial Ca2+ Fluxes, Biochem Pharmacol. 63, 247-250, 2002.
Sato T et al., Osteopontin/Eta-1 upregulated in Crohn's disease regulates the Th1 immune response. Gut. 54 (9):1254-62 (2005).

(56) References Cited

OTHER PUBLICATIONS

Seiler N et al., Polyamines and apoptosis. J Cell Mol Med. 9(3):623-642, 2005 J Cell Mol Med. Jul.-Sep. 2005; 9(3): 623-42.
Sherr et al., The FMS gene and the CSF-1 receptor. Cancer Surv. 5(2): 221-32 (1986).
Shevde LA et al., Osteopontin knockdown suppresses tumorigenicity of human metastatic breast carcinoma, MDA-MB-435. Clin Exp Metastasis 23(2): 123-33 (2006).
Siimes, M., Synergistic Action of 2 Polyamine Anti Metabolites leads to a Rapid Therapeutic Response in Childhood Leukemia, International Journal of Cancer, (1981) vol. 28, No. 5, pp. 567-570. CODEN: IJCNAW. ISSN: 0020-7136.
Simon M.S. et al., 'Phase II trial of methylglyoxal bis-guanylhydrazone (MGBG) in refractory small cell lung cancer', Investigational New Drugs, Martinus Nijhoff Publishers, Boston, US, (Jan. 1, 1990), vol. 8, ISSN 0167-6997, pp. S79-S81, XP008169410.
Singh, R. et al., Definition of a Specific Interaction Between the Early T Lymphocyte Activation 1 (Eta-1) Protein and Murine Macrophages in Vitro and its Effects Upon Macrophages in Vivo, J Exp Med. 171, 1931-1942, 1990.
Standal T et al., Role of osteopontin in adhesion, migration, cell survival and bone remodeling. Exp Oncol. 26(3): 179-84 (2004).
Takahashi F et al., Osteopontin is induced by nitric oxide in RAW 264.7 cells. IUBMB Life. 49: 217-221 (2000).
Takami, H., Experimental chronochemotherapy with methylglyoxal bis-(guanylhydrazone) (methyl-GAG), Proceedings of the American Association for Cancer Research, (1981) vol. vol. 22, pp. 882. CODEN: PAACA3.
Thiele, J. et al., Condensation Products of Aminoguanidine With Aldehydes and Ketones of the Aliphatic Series, Annalen Der Chemie 302, 275-299, 1898.
Thompson, H. et al., "History, Literature, and Theory of Enteric Coatings," 2006; Journal of the American Pharmaceutical Association, 34(5):135-138.
Tong, A. et al., "The Pathology of Atopic Dermatitis," 1986, Clin. Rev. Allergy, 4, pp. 27-42.
Tushinski RJ et al., The regulation of mononuclear phagocyte entry into S phase by the colony stimulating factor CSF-1. J Cell Physiol. 122(2): 221-8 (1985).
U.S. Appl. No. 13/865,816, Applicant-Initiated Interview Summary, dated Feb. 8, 2016, 3 pages.
U.S. Appl. No. 14/033,738, Examiner-Initiated Interview Summary, dated May 11, 2016, 1 page.
U.S. Appl. No. 14/033,738, Final Office Action, dated Sep. 15, 2015, 11 pages.
U.S. Appl. No. 14/033,738, Non-Final Office Action, dated Apr. 7, 2015, 13 pages.
U.S. Appl. No. 14/063,541, Affidavit-Traversing Rejections or Objections Rule 132, dated Nov. 5, 2015, 28 pages.
U.S. Appl. No. 14/063,541, Applicant-Initiated Interview Summary, dated Dec. 16, 2014, 3 pages.
U.S. Appl. No. 14/063,541, Final Office Action, dated May 5, 2015, 7 pages.
U.S. Appl. No. 14/063,541, Non-Final Office Action, dated Dec. 27, 2013, 8 pages.
U.S. Appl. No. 14/063,541, Non-Final Office Action, dated Aug. 14, 2014, 6 pages.
U.S. Appl. No. 14/063,541, Non-Final Office Action, dated May 5, 2016, 8 pages.
U.S. Appl. No. 14/458,919, Affidavit-Traversing Rejections or Objections Rule 132, dated Oct. 6, 2015, 8 pages.
U.S. Appl. No. 14/458,919, Final Office Action, dated Apr. 29, 2016, 18 pages.
U.S. Appl. No. 14/458,919, Non-Final Office Action, dated Apr. 6, 2015, 11 pages.
U.S. Pat. No. 8,258,186, Applicant-Initiated Interview Summary, dated May 16, 2012, 3 pages.
U.S. Pat. No. 8,258,186, Non-Final Office Action, dated Apr. 5, 2012, 7 pages.
U.S. Pat. No. 8,258,186, Notice of Allowance, dated Jun. 14, 2012, 7 pages.
U.S. Pat. No. 8,445,540, Final Office Action, dated Apr. 1, 2010, 12 pages.
U.S. Pat. No. 8,445,540, Non-Final Office Action, dated May 27, 2009, 12 pages.
U.S. Pat. No. 8,445,540, Notice of Allowance, dated Jan. 22, 2013, 8 pages.
U.S. Pat. No. 8,609,734, Applicant-Initiated Interview Summary, dated Dec. 12, 2013, 4 pages.
U.S. Pat. No. 8,609,734, Non-Final Office Action, dated Dec. 4, 2012, 9 pages.
U.S. Pat. No. 8,609,734, Notice of Allowance, dated Aug. 2, 2013, 6 pages.
U.S. Pat. No. 8,858,991, Applicant-Initiated Interview Summary, dated Dec. 23, 2013, 3 pages.
U.S. Pat. No. 8,858,991, Examiner-Initiated Interview Summary, dated Feb. 1, 2014, 1 page.
U.S. Pat. No. 8,858,991, Examiner-Initiated Interview Summary, dated Feb. 25, 2014, 2 pages.
U.S. Pat. No. 8,858,991, Final Office Action, dated Feb. 21, 2014, 16 pages.
U.S. Pat. No. 8,858,991, Non-Final Office Action, dated May 9, 2013, 18 pages.
U.S. Pat. No. 8,858,991, Notice of Allowance, dated Jun. 9, 2014, 10 pages.
Vogt et al., Elevated osteopontin levels in active relapsing-remitting multiple sclerosis. Ann Neurol. 53(6): 819-22 (2003).
Von Hoff et al, 'Methylglyoxal bis-guanylhydrazone in advanced bladder cancer', European Journal of Cancer and Clinical Oncology, Oxford, GB, vol. 26, No. 7, doi:DOI:10.1016/0277-5379(90)90171-O, ISSN 0277-5379, (Jan. 1, 1990), p. 848, (Jan. 1, 1990), XP026204322.
Von Hoff, D.D., "MGBG: Teaching an old drug new tricks," 1994, Annals of Oncology 5: 487-493.
Wallace HM et al., Inhibitors of polyamine metabolism: review article. Amino Acids. 26(4):353-65 (2004).
Webb et al., Direct observation and quantification of macrophage chemoattraction to the growth factor CSF-1. J Cell Sci. 109: 793-803 (1996).
Weber et al., Phosphorylation-Dependent Interaction of Osteopontin With its Receptors Regulates Macrophage Migration and Activation, J Leukoc Biol. 72, 752-761, 2002.
White, Florence R., 'Methyl-GAG', Cancer Bulletin, vol. 24, 1 pp. 79-84, XP009164055, ISSN: 0008-5448 Nov. 1962 (Nov. 1, 1962).
WO 2008/112659 International Preliminary Report on Patentability, dated Sep. 15, 2009, 6 pages.
WO 2008/112659 International Search Report, dated Sep. 2, 2008, 4 pages.
WO 2008/112659 Written Opinion, dated Sep. 2, 2008, 5 pages.
WO 2011/009039 International Preliminary Report on Patentability, dated Jan. 17, 2012, 7 pages.
WO 2011/009039 International Search Report, dated Apr. 25, 2011, 5 pages.
WO 2011/009039 Written Opinion, dated Apr. 25, 2011, 6 pages.
WO 2012/100043 International Preliminary Report on Patentability, dated Jul. 23, 2013, 8 pages.
WO 2012/100043 International Search Report, dated Aug. 7, 2012, 4 pages.
WO 2012/100043 Written Opinion, dated Aug. 7, 2012, 7 pages.
WO 2014/110154 International Preliminary Report on Patentability, dated Jul. 14, 2015, 6 pages.
WO 2014/110154 International Search Report, dated May 2, 2014, 6 pages.
WO 2014/110154 Written Opinion, dated May 2, 2014, 5 pages.
Wong CK et al., Elevation of plasma osteopontin concentration is correlated with disease activity in patients with systemic lupus erythematosus. Rheumatology (Oxford). 44(5): 602-6 (2005).
www.metrohealth.org (accessed online May 18, 2009), 2 pages.
Xu, G. et al., Role of Osteopontin in Amplification and Perpetuation of Rheumatoid Synovitis, J Clin Invest. 115(4), 1060-1067, 2005.
Yoshitake, H. et al., Osteopontin-Deficient Mice are Resistant to Ovariectomy-Induced Bone Resorption, PNAS 96, 8156-8160, 1999.

(56) References Cited

OTHER PUBLICATIONS

Yu, X. et al., A Functional Role for Osteopontin in Experimental Crescentic Glomerulonephritis in the Rat, Proc Assoc Am Physicians 110(1), 50-64, 1998.
Zhang, J. et al., The Role of Adenosine A2A and A2B Receptors in Regulation of TNF-alpha Production by Human Monocytes, Biochem Pharmacol. 69, 883-889, 2005.
Zhong, J. et al., Osteopontin Deficiency Protects Mice from Dextran Sodium Sulfate-Induced Colitis, Inflamm Bowel Dis. 12(8), 790-796, 2006.
Aher, et al., "Formulation Optimization and Pharmacokinetic Studies of an Enteric Coated Sustained Release Mucoadhesive Tablet of Zaltoprofen," Am. J. PharmTech Res., 4(4):133-62, (2014).
Allen, LV et al., Ansel's Pharmaceutical Dosage Forms and Drug Delivery Systems, 8th Edition, 1995, Lippincott Williams & Wilkins, Media, PA, pp. 260, 262 and 268-271.
Anonymous, "Cancer Chemotherapy Reports", JNCI: J Natl Cancer Inst, 22(2):441, (Feb. 1959).
Anonymous, "Naproxen Delayed Release", Drugs.com webpage at https://www.drugs.com/pro/naproxen-delayed-release.html, accessed Jul. 14, 2018; 33 pages, (2017).
Dutta, S. et al., "Distinct Absorption Characteristics of Oral Formulations of Valproic Acid/Divalproex Available in the United States", Epilepsy Res., 73(3):275-83, (2007).
Holland, J. et al., "Growth Inhibitors of Transplanted Rodent Tumors by Glyoxal-bis-guanylhydrazones", Cancer Research (Suppl.), 21: No. 3, Part 2, pp. 15-26, 1961.
Howden, "Review Article: Immediate-Release Proton-Pump Inhibitor Therapy—Potential Advantages", Alimentary Pharmacol. Therapeutics, 22(Suppl. 3):25-30, (2005).
International Application No. PCT/US2014/010714; International Preliminary Report on Patentability, dated May 2, 2014; 6 pages.
International Application No. PCT/US2014/010714; International Search Report and Written Opinion of the International Search Authority, dated May 2, 2014; 11 pages.
Khan, M. et al., "A pH-dependent colon targeted oral drug delivery system using methacrylic acid copolymers. I. Manipulation of drug release using Eudragit L100-55 and Eudragit S100 combinations", J Control Release., 58 (2):215-22, (1999).
Kim, Y. et al., "Preparation and Evaluation of Enteric-Coated Delayed-Release Pellets of Duloxetine Hydrochloride Using a Fluidized Bead Coater", Archives of Pharmacol. Res., 38(12):2163-71, (2015).
Licht, D. et al., "Is it Possible to Achieve Bio-Equivalence Between an Oral Solid Immediate-Release and an Analogue Enteric-Coated Formulation?", J. Pharmacy and Pharmacol., 68(10):1278-89, (2016).
Schilling, S. et al., "Fumaric Acid Esters are Effective in Chronic Experimental Autoimmune Encephalomyelitis and Suppress Macrophage Infiltration", Clin. Exp Immunol. 145(1):101-7, (Jul. 2006).
U.S. Appl. No. 12/837,753; First Action Interview—office action dated Apr. 27, 2012; 2 pages.
U.S. Appl. No. 13/865,816; Affidavit-traversing rejections or objections rule 132 dated Jan. 27, 2017; 28 pages.
U.S. Appl. No. 13/865,816; First Action Interview—office action dated Oct. 2, 2015; 3 pages.
U.S. Appl. No. 13/865,816; Notice of Allowance dated Sep. 12, 2017; 9 pages.
U.S. Appl. No. 14/033,738; Notice of Allowance dated Feb. 13, 2017; 6 pages.
U.S. Appl. No. 14/033,738; Notice of Allowance dated Feb. 28, 2017; 4 pages.
U.S. Appl. No. 14/063,541; Notice of Allowance dated Nov. 23, 2016; 8 pages.
U.S. Appl. No. 14/458,919; Non-Final Office Action dated May 12, 2017; 13 pages.
U.S. Appl. No. 14/480,847; Examiner Initiated Interview Summary dated Jan. 30, 2017; 2 pages.
U.S. Appl. No. 14/480,847; Non-Final Office Action dated Jun. 28, 2016; 15 pages.
U.S. Appl. No. 14/480,847; Notice of Allowance dated Jan. 30, 2017; 8 pages.
U.S. Appl. No. 14/759, 599; Non-Final Office Action dated Jun. 6, 2016; 7 pages.
U.S. Appl. No. 14/759,599; Final Office Action dated Feb. 27, 2017; 6 pages.
U.S. Appl. No. 14/759,599; Non-Final Office Action dated Oct. 5, 2017; 8 pages.
U.S. Appl. No. 14/759,599; Notice of Allowance dated May 21, 2018; 7 pages.
U.S. Appl. No. 15/441,122; Non-Final Office Action dated Sep. 13, 2018; 37 pages.
U.S. Appl. No. 15/583,697; Advisory Action, dated Oct. 5, 2018; 19 pages.
U.S. Appl. No. 15/583,697; Applicant-Initiated Interview Summary dated Jul. 13, 2018, 2 pages.
U.S. Appl. No. 15/583,697; Final Office Action dated Jun. 28, 2018; 24 pages.
U.S. Appl. No. 15/583,697; Non-Final Office Action dated Mar. 2, 2018; 11 pages.
U.S. Appl. No. 16/109,824; Application as filed dated Aug. 23, 2018; 171 pages.
Wagner, CA et al., Novel Insights and Therapeutics in Multiple Sclerosis [v1; ref status: indexed, http://f1000r.es/59z]F1000Research 2015, 4(F1000 Faculty Rev):517 (doi: 10.12688/f1000research.6378.1).
Wang, X., "Diffusion Tensor Imaging Detects Treatment Effects of FTY720 in Experimental Autoimmune Encephalomyelitis Mice", NMR Biomed. 26(12):1742-50, (Aug. 2013).
Zagon, I. et al., Multiple Sclerosis: Perspectives in Treatment and Pathogenesis, Department of Neural & Behavioral Sciences, Pennsylvania State University College of Medicine, Hershey, Pennsylvania, USA, 2017, 204 pages.
Zhao, et al., "Pharmacokinetics of Rhein Enteric-Coated Sustained-Release Pellets in Rabbits", Zhongguo Shiyan Fangjixue Zazhi, 19(8):159-62, (2013), (Abstract only).
Ziemssen, T. et al., Evaluation of Study and Patient Characteristics of Clinical Studies in Primary Progressive Multiple Sclerosis: A Systematic Review, PLOS One, 2015, 22 pages.
U.S. Appl. No. 16/109,824; Non-Final Office Action dated Feb. 14, 2019; 18 pages.
Dal Canto, M. et al., "Two Models of Multiple Sclerosis: Eperimental Allergic Encephalomyelitis (EAE) and Theiler's Murine Encephalomyelitis Virus (TMEV) Infection. A Pathological and Immunological Comparison", Microsc Res Tech., 32(3):215-29, (1995).
Kapoor, S., "Osteopontin: A Major Player in the Pathogenesis of Endocrine and Systemic Diseases", Endocr J., 55 (4):785, (2008).
Racke, M. et al., "Nuclear Receptors and Autoimmune Disease: The Potential of PPAR Agonists to Treat Multiple Sclerosis", J Nutr., 136(3):700-3, (2006).
Steinman, L. et al., "New Targets for Treatment of Multiple Sclerosis", J Neurol Sci., 274(1-2)1-4, (2008).

* cited by examiner

A placebo (left)
MGBG (center)
naproxen (right)

B

C

METHOD OF TREATMENT WITH ANTI-INFLAMMATORY AND ANALGESIC COMPOUNDS WHICH ARE GI-, RENAL-, AND PLATELET-SPARING

This application is a continuation of U.S. application Ser. No. 14/033,738, filed Sep. 23, 2013, which is a continuation-in-part of U.S. application Ser. No. 13/556,948, filed Jul. 4, 2012, now U.S. Pat. No. 8,609,734, issued on Dec. 17, 2013, which is a continuation of U.S. application Ser. No. 12/837,753, filed Jul. 16, 2010, now U.S. Pat. No. 8,258,186, issued on Sep. 4, 2012, which claims the benefit of priority of U.S. provisional application Nos. 61/226,060, filed Jul. 16, 2009, and 61/290,095, filed Dec. 24, 2009, and also claims the benefit of priority of U.S. provisional application No. 61/704,104, filed Sep. 21, 2012, the disclosures of which are incorporated by reference as if written herein in their entirety.

There is an explicit need for effective but safer analgesic and anti-inflammatory agents, particularly drugs that do not inhibit either form of cyclooxygenase. Patients with decreased renal function, gastrointestinal sensitivity such as peptic ulcer disease, or increased risk for bleeding cannot take most non-steroidal anti-inflammatory drugs (NSAIDs), the largest class of anti-inflammatory/analgesics currently available—all of which inhibit one or both forms of cyclooxygenase. Additionally, acetaminophen (paracetamol), a non-NSAID, non-opioid pain drug which is not a blood thinner, is not ideal because it has only weak anti-inflammatory activity and is both acutely hepatotoxic as well as potentially nephrotoxic.

Intravenous formulations of methylglyoxal-bisguanylhydrazone (MGBG) have been previously tested in the clinic given the compound's inhibitory activity against S-adenosylmethionine decarboxylase (SAMDC), a key enzyme mediating the biosynthesis of cell growth-promoting polyamines (spermine and spermidine). MGBG selectively distributes to and functionally inactivates monocytes/macrophages, cells critical to inflammation and pain. Additionally, in contrast to decades of literature teaching parenteral administration, pharmacokinetic (PK) studies using current LC/MS/MS-based bioanalytics have demonstrated that MGBG is orally bioavailable.

It has now been discovered that oral MGBG is gastrointestinal-tissue-sparing, renal-sparing, and platelet-sparing, and does not inhibit either form of cyclooxygenase. Thus, polyamine analogs, such as MGBG, are well-suited for use in the treatment of pain and inflammation in those patients who cannot tolerate NSAIDS due to gastrointestinal sensitivity such as that caused by peptic ulcer disease, decreased renal function, or increased risk for bleeding.

Accordingly, disclosed herein are compounds, pharmaceutical compositions, and methods for the treatment of diseases such as inflammation and/or pain, comprising the administration of a therapeutically effective amount of a compound having GI-/renal-/platelet-sparing activities, and wide safety margins with no appreciable inhibition of either form of cyclooxygenase. Polyamine analogs and polyamine biosynthesis inhibitors have been discovered which possess these properties. For example, the SAMDC inhibitor MGBG could have comparable efficacy to the leading anti-inflammatory/analgesic drugs on the market without sharing their fundamental safety liabilities.

Figure 1:
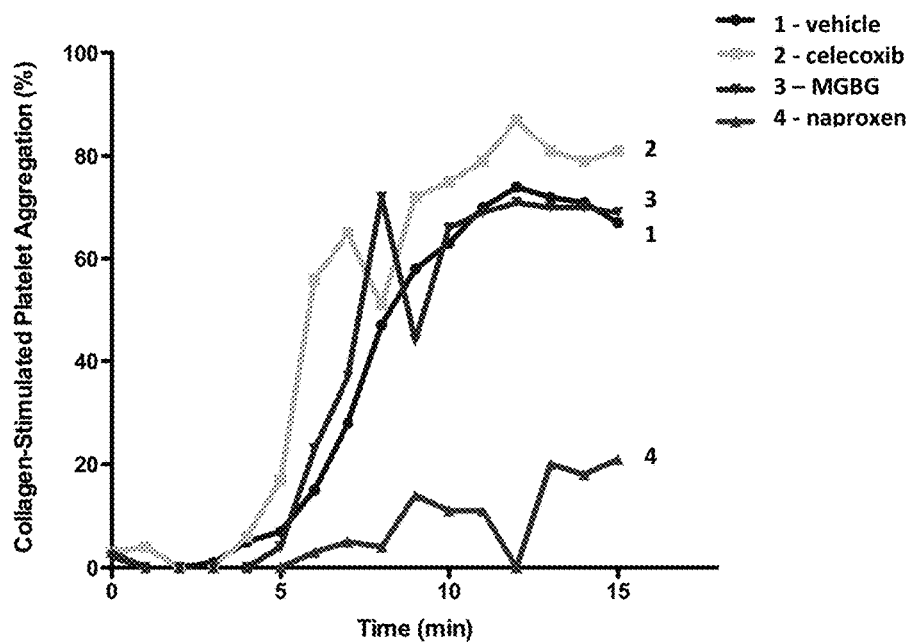
FIG. 1 shows the effect of high-dose oral MGBG, compared to naproxen, celecoxib, and vehicle, on platelet aggregation.

Provided herein is a method of treatment of pain or inflammation in a patient in need thereof, comprising administering a therapeutically effective amount of an analgesic, anti-inflammatory compound, wherein the compound does not inhibit cyclooxygenase and is not an opioid, and is gastrointestinal-, platelet-, and renal-sparing.

In certain embodiments, the compound is a polyamine analog or polyamine biosynthesis inhibitor.

In certain embodiments, the compound is a SAMDC inhibitor.

In certain embodiments, the compound is MGBG.

In certain embodiments, the compound is formulated for oral delivery.

In certain embodiments, the compound is formulated for delayed-release oral delivery to the small bowel.

In certain embodiments, NSAID drugs are not advisable or contraindicated in the patient.

In certain embodiments, the patient has a bleeding, clotting, gastrointestinal, or renal disorder, a disease where sodium/fluid retention would be undesirable, or severe hepatic impairment or advanced liver disease. Such patients tend to have low platelets (secondary to hypersplenism), prolonged prothrombin time/INR (secondary to deficiency in the vitamin K-dependent clotting factors), and varices (particularly esophageal varices at risk for bleeding).

In certain embodiments, the disorder is chosen from hemophilia, peptic ulcer, renal insufficiency CHF, hypertension, and chronic kidney disease.

Also provided is a method of treatment of pain or inflammation in an elderly patient in need thereof, comprising administering a therapeutically effective amount of an analgesic, anti-inflammatory compound, wherein the compound does not inhibit cyclooxygenase and is not an opioid or a steroid, and is gastrointestinal-, platelet-, and renal-sparing.

In certain embodiments, the patient is over 50 years of age.

In certain embodiments, the patient is over 55 years of age.

In certain embodiments, the patient is over 60 years of age.

In certain embodiments, the patient is over 65 years of age.

In certain embodiments, the patient is over 70 years of age.

In certain embodiments, the compound is a polyamine analog or polyamine biosynthesis inhibitor.

In certain embodiments, the compound is a SAMDC inhibitor.

In certain embodiments, the compound is MGBG.

In certain embodiments, the compound is formulated for oral delivery.

In certain embodiments, the compound is formulated for delayed-release oral delivery to the small bowel.

Also provided is a method of treatment of pain or inflammation in a patient with a history of peptic ulcer disease or at increased risk of GI bleeding/ulceration/obstruction and in need of such treatment, comprising administering a therapeutically effective amount of an analgesic, anti-inflammatory compound, wherein the compound does not inhibit cyclooxygenase and is not an opioid or a steroid, and is gastrointestinal-, platelet-, and renal-sparing.

In certain embodiments, the compound is a polyamine analog or polyamine biosynthesis inhibitor.

In certain embodiments, the compound is a SAMDC inhibitor.

In certain embodiments, the compound is MGBG.

In certain embodiments, the compound is formulated for oral delivery.

In certain embodiments, the compound is formulated for delayed-release oral delivery to the small bowel.

Also provided is a method of treatment of pain or inflammation in a renally-impaired patient in need thereof, comprising administering a therapeutically effective amount of an analgesic, anti-inflammatory compound, wherein the compound does not inhibit cyclooxygenase and is not an opioid or a steroid, and is gastrointestinal-, platelet-, and renal-sparing.

In certain embodiments, the patient has a renal disease, congestive heart failure, or cirrhosis, or is volume-depleted or dehydrated.

Also provided is a method of treatment of pain or inflammation in a patient with an increased risk for bleeding in need thereof, comprising administering a therapeutically effective amount of an analgesic, anti-inflammatory compound, wherein the compound does not inhibit cyclooxygenase and is not an opioid or a steroid, and is gastrointestinal-, platelet-, and renal-sparing.

In certain embodiments, the patient with an increased risk for bleeding is taking an anti-coagulant drug, has cirrhosis or thrombocytopenia, or who is pre-operative for surgery.

In certain embodiments, the compound is a polyamine analog or polyamine biosynthesis inhibitor.

In certain embodiments, the compound is a SAMDC inhibitor.

In certain embodiments, the compound is MGBG.

In certain embodiments, the compound is formulated for oral delivery.

In certain embodiments, the compound is formulated for delayed-release oral delivery to the small bowel.

Also provided is a method of treatment of pain or inflammation in a patient with a bleeding or clotting disorder in need thereof, comprising administering a therapeutically effective amount of an analgesic, anti-inflammatory compound, wherein the compound does not inhibit cyclooxygenase and is not an opioid or a steroid, and is gastrointestinal-, platelet-, and renal-sparing.

In certain embodiments, the patient with a bleeding or clotting disorder is taking an anti-coagulant drug, has cirrhosis or thrombocytopenia, or who is pre-operative for surgery.

In certain embodiments, the compound is a polyamine analog or polyamine biosynthesis inhibitor.

In certain embodiments, the compound is a SAMDC inhibitor.

In certain embodiments, the compound is MGBG.

In certain embodiments, the compound is formulated for oral delivery.

In certain embodiments, the compound is formulated for delayed-release oral delivery to the small bowel.

As used herein, the terms below have the meanings indicated.

The term "activity" as used herein in connection with osteopontin refers to both, the biological activity of the polypeptide and to the quantity or level of osteopontin present in the cell. In one embodiment, the term activity refers to the quantity of osteopontin, e.g., present, expressed or produced in the cell. In another embodiment, it refers to the level of osteopontin secreted by the cell, for example, by a mononuclear cell.

When ranges of values are disclosed, and the notation "from n1 . . . to n2" or "between n1 . . . and n2" is used, where n1 and n2 are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 µM (micromolar)," which is intended to include 1 µM, 3 µM, and everything in between to any number of significant figures (e.g., 1.255 µM, 2.1 µM, 2.9999 µM, etc.).

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "substantially" as used herein is intended to mean predominantly or having the overriding characteristic of, such that any opposing or detracting characteristics reach a level of insignificance. By way of example, a composition "substantially" free of water might not be absolutely free of all traces of water, but would be sufficiently anhydrous that any remaining water would not influence the composition in any significant way. By way of further example, "substantially dose-limiting side effects" might be side effects which limited a dose to a level which was below that required for therapeutic efficacy.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

As used herein, "hyperalgesia" means a heightened sensitivity to pain, and can be considered a type of pain or a measure of pain-related behavior.

As used herein, reference to "treatment" of a patient is intended to include prophylaxis. Treatment may also be preemptive in nature, i.e., it may include prevention of disease. Prevention of a disease may involve complete protection from disease, for example as in the case of prevention of infection with a pathogen, or may involve prevention of disease progression. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

The term "patient" is generally synonymous with the term "subject" and means an animal differing from a disease, disorder, or condition treatable in accordance with the methods disclosed herein, including all mammals and humans. Examples of patients include humans, livestock such as cows, goats, sheep, pigs, and rabbits, and companion animals such as dogs, cats, rabbits, and horses. Preferably, the patient is a human.

An "effective amount" or a "therapeutically effective amount" is a quantity of a compound (e.g., MGBG, a polyamine analog, a polyamine biosynthesis inhibitor or any agent) that is sufficient to achieve a desired effect in a subject being treated. For instance, this can be the amount necessary to treat a disease, disorder, condition, or adverse state (such as pain or inflammation) or to otherwise measurably alter or alleviate the symptoms, markers, or mechanisms of the disease, disorder, condition, or adverse state. As just one example, an effective amount for the treatment of pain is an amount sufficient to prevent, delay the onset of, or reduce pain or one or more pain-related symptoms in a subject, as measured by methods known in the art. Similar methods of assessing response to treatment of a number of diseases are well-known in the art. The effective amount of a compound of the present invention may vary depending upon the route of administration and dosage form. In addition, specific dosages may be adjusted depending on conditions of disease, the age, body weight, general health conditions, sex, and diet of the subject, dose intervals, administration routes, excretion rate, and combinations of agents.

The term "low dose," in reference to a low dose formulation of a drug or a method of treatment specifically employing a "low dose" of a drug, means a dose which for at least one indication is subtherapeutic, or is a fraction of the dose typically given for at least one indication. Take for example the case of a drug for the treatment of proliferative disorders—a low dose formulation for the treatment of, say, chronic psoriasis, might be a fraction of the dose for the treatment of an aggressive cancer. In this way, the dose for one disease might be an amount which would be subtherapeutic for another disease. Alternatively, for a drug which is therapeutic in different individuals or populations at different doses, and is available in a range of doses, a low dose may be simply a dose toward the low end of recognized therapeutic efficacy. Chronic diseases represent an embodiment treatable by low dose formulations and methods. Additionally, a subtherapeutic amount of a drug might be used in combination with one or more other drugs (themselves in either therapeutic or subtherapeutic amounts) to yield a combination formulation or treatment which is potentiated, that is, more efficacious than the expected effects of the sum of the drugs given alone. A low dose for the treatment of one indication may be two-fold, three-fold, four-fold, five-fold, six-fold, seven-fold, eight-fold, nine-fold, ten-fold, fifteen-fold, twenty-fold, thirty-fold, forty-fold, fifty-fold, may be one hundred-fold less than the therapeutic dose for a different indication.

The phrase "therapeutically effective" is intended to qualify the amount of active ingredients used in the treatment of a disease or disorder or on the effecting of a clinical endpoint.

The term "therapeutically acceptable" refers to those compounds (or salts, prodrugs, tautomers, zwitterionic forms, etc.) which are suitable for use in contact with the tissues of subjects without undue toxicity, irritation, and allergic response, are commensurate with a reasonable benefit/risk ratio, and are effective for their intended use.

The term "drug" is used herein interchangeably with "compound" and "agent."

As used herein, a "polyamine" is any of a group of aliphatic, straight-chain amines derived biosynthetically from amino acids; polyamines are reviewed in Marton et al. (1995) Ann. Rev. Pharm. Toxicol. 35:55-91. By "polyamine" is generally meant a naturally-occurring polyamine or a polyamine which is naturally produced in eukaryotic cells. Examples of polyamines include putrescine, spermidine, spermine and cadaverine.

As used herein, a "polyamine analog" is an organic cation structurally similar but non-identical to naturally-occurring polyamines such as spermine and/or spermidine and their precursor, diamine putrescine. Polyamine analogs can be branched or un-branched, or incorporate cyclic moieties. Polyamines may comprise primary, secondary, tertiary, or quaternary amino groups. In one embodiment, all the nitrogen atoms of the polyamine analogs are independently secondary, tertiary, or quaternary amino groups, but are not so limited. Polyamine analogs may include imine, amidine and guanidine groups in place of amine groups. The term "polyamine analog" includes stereoisomers, salts and protected derivatives of polyamine analogs.

A "stereoisomer" is any optical isomer of a compound, including enantiomers and diastereomers. Unless otherwise indicated, structural formulae of compounds are intended to embrace all possible stereoisomers.

A "salt" or "pharmaceutically acceptable salt" is a compound formed by the replacement of one or more hydrogen atoms with elements or groups, which is composed of anions and cations, which usually ionizes in water; a salt is formed, for instance, by neutralization of an acid by a base. Examples of salts include, but are not limited to, halide, for example, chloride, bromide, or iodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts.

"Protected derivative" is used to refer to a compound protected with a protecting group. "Protecting group" refers to a chemical group that exhibits the following characteristics: 1) reacts selectively with the desired functionality in good yield (preferably at least 80%, more preferably at least 90%, more preferably at least 95%, still more preferably at least 99%) to give a protected substrate that is stable to the projected reactions for which protection is desired; 2) is selectively removable from the protected substrate to yield the desired functionality; and 3) is removable in good yield (preferably at least 80%, more preferably at least 90%, more preferably at least 95%, still more preferably at least 99%) by reagents compatible with the other functional group(s) present or generated in such projected reactions. Examples of suitable protecting groups can be found in Greene et al. (1991) Protective Groups in Organic Synthesis, 2nd Ed. (John Wiley & Sons, Inc., New York). Exemplary protecting groups for the amino functionality include, but are not limited to, mesitylenesulfonyl (MesS02), benzyloxycarbonyl (CBz), t-butyloxycarbonyl (Boc), t-butyldimethylsilyl (TBDIMS), 9-fluorenylmethyloxycarbonyl (Fmoc), or suitable photolabile protecting groups such as 6-nitroveratryloxy carbonyl (Nvoc).

The term "gastrointestinal-, platelet-, and renal-sparing," as used herein, means that the compound does not cause or exacerbate harmful side effects in the gastrointestinal or renal system, and does not inhibit platelet aggregation.

The compounds, compositions, and methods disclosed herein may be useful in patients for whom NSAID drugs are not advised or explicitly contraindicated. Such patients include those with a bleeding, clotting, gastrointestinal, or renal disorder, pre-operative patients, and the elderly in general. NSAIDs are often avoided due to their GI, renal, or platelet side effects. For example, NSAIDs should be avoided due to their GI side effects in patients with history of peptic ulcer disease or at increased risk of GI bleeding/ulceration/obstruction—particularly the elderly—and in patients who are intolerant of NSAIDs (e.g. who have dyspepsia). NSAIDs should be avoided due to their renal side effects: a) in patients with pre-existing renal disease/CHF/cirrhosis or who are volume-depleted/dehydrated (to prevent acute renal failure) b) in elderly patients with age-related decreased glomerular filtration rate (GFR); and c) where there is an increased risk in patients with hypertension. NSAIDs should be avoided due to their platelet effects in patients taking anti-coagulants, in patients with cirrhosis or thrombocytopenia, or in patients who are pre-operative for surgery; one exception here, however, is for aspirin in heightened cases of cardiovascular risk given its cardioprotective properties.

The compounds, compositions, and methods disclosed herein may be useful in patients with renal insufficiency or disorders of renal perfusion (e.g. CHF). Renal insufficiency may be due to acute kidney injury (AKI, previously called acute renal failure or ARF), acute-on-chronic renal failure (AoCRF), or chronic kidney disease (CKD).

Causes of acute kidney injury include prerenal, intrinsic, and postrenal causes, including: acute low blood volume or low blood pressure, heart failure, aneurysm, renal artery stenosis, renal vein thrombosis, renal ischemia, glomerulonephritis, acute tubular necrosis (ATN), acute interstitial nephritis (AIN), tumour lysis syndrome, rhabdomyolysis, and urinary tract obstruction such as from benign prostatic hyperplasia or kidney stones.

Chronic kidney disease includes, or may be caused by: diabetes mellitus; hypertension; glomerulonephritis, including primary glomerular disease such as focal segmental glomerulosclerosis and IgA nephritis, and secondary glomerular disease such as diabetic nephropathy and lupus nephritis; large vessel disease such as bilateral renal artery stenosis and small vessel disease such as ischemic nephropathy, hemolytic-uremic syndrome and vasculitis; tubulointerstitial disorders including polycystic kidney disease, drug and toxin-induced chronic tubulointerstitial nephritis, and reflux nephropathy; obstructive problems such as with bilateral kidney stones and diseases of the prostate; and infection of the kidney with pathogens or parasites which cause nephropathy; and neoplasia.

Additionally, the compounds, compositions, and methods disclosed herein may be useful in patients who have increased sodium retention or an increased sensitivity to sodium, such as patients with hypertension, congestive heart failure (CHF), and advanced liver disease. NSAID drugs inhibit sodium excretion, which makes them a poor choice.

Additionally, the compounds, compositions, and methods disclosed herein may be useful in patients with bleeding or clotting disorders, or with an increased risk for bleeding, for whom platelet aggregation may be negatively affected by the administration of an NSAID drug. Examples of such diseases include hemophilia and Von Willebrand disease.

Additionally, the compounds, compositions, and methods disclosed herein may be useful in pre-operative patients.

Additionally, the compounds, compositions, and methods disclosed herein may be useful in patients taking anti-coagulants, such as Coumadin or heparin.

Additionally, the compounds, compositions, and methods disclosed herein may be useful in patients with gastrointestinal (GI) sensitivity or a GI disorder such as peptic ulcer.

Dosage

The proper dose of the compounds disclosed herein depends on a number of factors. The average body weight of a normal male human is often presumed to be 70 kg. Thus, daily doses based on the predictions discussed below could be estimated to range from about 25 mg/day to about 350 mg/day. The patient may weigh much more or much less, or be female, elderly, or juvenile, requiring a lower or higher dose. The patient may exhibit a drug metabolic profile which might counsel for a lower or higher dose, such as a low expression level or activity of metabolizing enzymes. Alternatively, the patient may be physically weak, injured, or immunocompromised, all of which might counsel a lower dose. The patient may be taking a number of other drugs which compete with metabolic systems for disposal; this well-known polypharmaceutical effect may call for a lower dose. The dose also depends, as discussed above, on the condition and its severity. The efficacious dose for one disease or clinical endpoint will not necessarily be the same as the dose for another, and a severe, chronic, or otherwise serious case may call for a higher dose. However, a chronic case may also call for a lower dose administered over a longer or even indefinite period of time. All of these are discussed by way of example to illustrate the variability of ideal dosing; it is within the capacity of the skilled artisan to select an appropriate dosing range for a disease, population, or individual.

With these factors in mind, it should be clear that it is possible that the daily human dose may be as low as 1 mg/day, and as high as a 1 g/day. In certain embodiments, the human dose may range: from 10 mg/day to 500 mg/day, from 20 mg/day to 400 mg/day, or from 25 mg/day to 350 mg/day. In further embodiments, the human dose may range from 120 mg/day to 350 mg/day, from 150 mg/day to 350 mg/day, from 200 mg/day to 350 mg/day, or from 250 mg/day to 350 mg/day. In certain embodiments, the human dose may be any one of 1, 2, 3, 4, 5, 6, 7, 8, 9, 10, 12, 15, 20, 25, 30, 35, 40, 45, 50, 55, 60, 65, 70 75, 80, 85, 90, 95, 100, 110, 120, 125, 130, 140, 150, 160, 170, 175, 180, 190, 200, 210, 220, 225, 230, 240, 250, 260, 270, 275, 280, 290, 300, 310, 320, 325, 330, 340, or 350 mg/day.

In certain embodiments, the human dose may be any one of 275, 280, 285, 290, 295, 300, 305, 310, 315, 320, 325, 330, 335, 340, 350, 355, 360, 365, 370, or 375 mg/day. In one embodiment, the dose may be 275 mg/day. In another embodiment, the dose may be 300 mg/day. In another embodiment, the dose may be 305 mg/day. In another embodiment, the dose may be 310 mg/day. In another embodiment, the dose may be 315 mg/day. In another embodiment, the dose may be 320 mg/day. In another embodiment, the dose may be 325 mg/day. In another embodiment, the dose may be 330 mg/day. In another embodiment, the dose may be 335 mg/day. In another embodiment, the dose may be 340 mg/day. In another embodiment, the dose may be 345 mg/day. In another embodiment, the dose may be 350 mg/day.

In certain embodiments, the human dose may be any one of 350, 375, 400, 425, 450, 475, 500, 525, 550 or 600 mg/day. In one embodiment, the dose may be 375 mg/day.

In another embodiment, the dose may be 400 mg/day. In another embodiment, the dose may be 450 mg/day. In another embodiment, the dose may be 500 mg/day.

In certain embodiments, the human dose may be any one of 25, 50, 75, 100, or 125 mg/day. In one embodiment, the dose may be 375 mg/day. In another embodiment, the dose may be 25 mg/day. In another embodiment, the dose may be 50 mg/day. In another embodiment, the dose may be 75 mg/day. In another embodiment, the dose may be 100 mg/day. In another embodiment, the dose may be 125 mg/day.

Combination Therapy

In certain instances, it may be appropriate to administer at least one of the compounds described herein (or a pharmaceutically acceptable salt, ester, or prodrug thereof) in combination with another therapeutic agent. By way of example only, if one of the side effects experienced by a subject upon receiving one of the compounds herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the subject is enhanced). Or, by way of example only, the benefit experienced by a subject may be increased by administering one of the compounds described herein with another therapeutic agent (which also includes a therapeutic regimen) that also has therapeutic benefit. By way of example only, in a treatment for neuropathy involving administration of one of the compounds described herein, increased therapeutic benefit may result by also providing the subject with another therapeutic agent for neuropathy. In any case, regardless of the disease, disorder or condition being treated, the overall benefit experienced by the subject may simply be additive of the two therapeutic agents or the subject may experience a synergistic benefit.

Examples of agents for use in combination may be found in, for example, U.S. patent application Ser. No. 12/837,753, filed Jul. 16, 2010, now issued as U.S. Pat. No. 8,258,186, the disclosures of which are incorporated by reference as if written herein in their entireties.

In any case, the multiple therapeutic agents (at least one of which is a compound disclosed herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the doses of the multiple therapeutic agents may be any duration of time ranging from a few minutes to four weeks.

Thus, in another aspect, certain embodiments provide methods for treating disorders in a human or animal subject in need of such treatment comprising administering to said subject an amount of a compound disclosed herein effective to reduce or prevent said disorder in the subject, optionally in combination with at least one additional agent for the treatment of said disorder that is known in the art. Specific diseases to be treated by the compounds, compositions, and methods disclosed herein, singly or in combination, include, without limitation: pain; neuropathy; inflammation and related disorders; arthritis; metabolic inflammatory disorders; respiratory disorders; autoimmune disorders; neurological disorders; and proliferative disorders, including cancer and non-cancerous diseases.

The compounds disclosed herein are useful to treat patients with pain, including neuropathy and/or neuropathic pain, and inflammatory pain. Pain indications include, but are not limited to, treatment or prophylaxis of surgical or post-surgical pain for various surgical procedures including amputation, post-cardiac surgery, dental pain/dental extraction, pain resulting from cancer, muscular pain, mastalgia, pain resulting from dermal injuries, lower back pain, headaches of various etiologies, including migraine, menstrual cramps, and the like. The compounds are also useful for the treatment of pain-related disorders such as tactile allodynia and hyperalgesia. The pain may be somatogenic (either nociceptive or neuropathic), acute and/or chronic.

Other disorders or conditions which can be advantageously treated by the compounds disclosed herein include inflammation and inflammatory conditions. Inflammatory conditions include, without limitation: arthritis, including sub-types and related conditions such as rheumatoid arthritis, spondyloarthropathies, gouty arthritis, osteoarthritis, systemic lupus erythematosus, juvenile arthritis, acute rheumatic arthritis, enteropathic arthritis, neuropathic arthritis, psoriatic arthritis, and pyogenic arthritis; osteoporosis, tendonitis, bursitis, and other related bone and joint disorders; gastrointestinal conditions such as reflux esophagitis, diarrhea, inflammatory bowel disease, Crohn's disease, gastritis, irritable bowel syndrome, ulcerative colitis, acute and chronic inflammation of the pancreas; pulmonary inflammation, such as that associated with viral infections and cystic fibrosis; skin-related conditions such as psoriasis, eczema, burns, sunburn, dermatitis (such as contact dermatitis, atopic dermatitis, and allergic dermatitis), and hives; pancreatitis, hepatitis, pruritis and vitiligo. In addition, compounds of invention are also useful in organ transplant patients either alone or in combination with conventional immunomodulators.

Autoimmune disorders may be ameliorated by the treatment with compounds disclosed herein. Autoimmune disorders include Crohns disease, ulcerative colitis, dermatitis, dermatomyositis, diabetes mellitus type 1, Goodpasture's syndrome, Graves' disease, Guillain-Barré syndrome (GBS), autoimmune encephalomyelitis, Hashimoto's disease, idiopathic thrombocytopenic purpura, lupus erythematosus, mixed connective tissue disease, multiple sclerosis (MS), myasthenia gravis, narcolepsy, pemphigus vulgaris, pernicious anemia, psoriasis, psoriatic arthritis, polymyositis, primary biliary cirrhosis, rheumatoid arthritis, Sjögren's syndrome, scleroderma, temporal arteritis (also known as "giant cell arteritis"), vasculitis, and Wegener's granulomatosis. The compounds disclosed herein may regulate TH-17 (T-helper cells producing interleukin 17) cells or IL-17 levels.

Additional diseases and conditions in which the compounds, compositions and methods disclosed herein are useful may be found in, for example, U.S. patent application Ser. No. 12/837,753, filed Jul. 16, 2010, now issued as U.S. Pat. No. 8,258,186, the disclosures of which are incorporated by reference as if written herein in their entireties.

Compound Examples

Compounds disclosed herein useful according to the various embodiments of the present invention include polyamine analogs and polyamine biosynthesis inhibitors. In certain embodiments, the compound inhibits the activity of S-adenosyl methionine decarboxylase (SAMDC), or otherwise inhibits polyamine biosynthesis.

Examples of such compounds include, but are not limited to, those listed in Table 1. Irrespective of the form of the moiety listed in Table 1, it is understood that it includes, as applicable, a salt, protected derivative, and stereoisomer thereof. The following compounds may be made by methods known in the art, and in some cases may be commercially available.

TABLE 1

| Compound | Official Name (Not IUPAC) | Pub Chem ID |
|---|---|---|
| Decarboxylated SAM | s-adenosyl-3-methylthiopropylamine | 5351154 |
| Mitoguazone or "MGBG" | Methylglyoxal bis(guanylhydrazone) | 9561662 |
| EGBG | Ethylglyoxal bis(guanylhydrazone) | 2354 |
| Berenil | Diminazene or Diminazene aceturate | 4735 |
| Pentamidine | 4-[5-(4-carbamimidoylphenoxy)pentoxy] benzenecarboximidamide | |
| | 5'-(Dimethylsulphino)-5'-deoxyadenosine | |
| | S-adneosyl-4-methylthiobutyrate | |
| | S-adenosyl-S-methyl-L-cysteine | |
| AMA | S-(5'-Deoxy-5'-adenosyl) methylthioethylhydroxylamine | |
| EMGBG | Ethylmethylglyoxal bis(guanylhydrazone) | |
| DEGBG | Diethylglyoxal bis(guanylhydrazone) | 9574151 |
| CGP-33'829 | 6-((2-carbamimidoylhydrazono)methyl) picolinimidamide | 5479208 |
| CGP-36'958 | | |
| CGP-39'937 | 2,2'-bipyridine-6,6'-bis(carboximidamide) | |
| CGP-48664 or CGP48664A or SAM 364A | 4-amidinoindan-1-one 2'-amidinohydrazone | 5486811 |
| AbeAdo or MDL-73811 | 5'-[[(Z)-4-amino-2-butenyl] methylamino]-5'-deoxyadenosine | 6436013 |
| MAOEA | 5'-deoxy-5'-[N-methyl-N-[2-(aminooxy)ethyl]amino]adenosine | 3081018 |
| MHZPA | 5'-deoxy-5'-[N-methyl-N-(3-hydrazinopropyl)amino]adenosine | 122092 |
| MHZEA | 5'-deoxy-5'-[(2-hydrazinoethyl)-methylamino]adenosine | |
| AdoMac | S-(5'-deoxy-5'-adenosyl)-1-ammonio-4-(methylsulfonio)-2cyclopentene | 3083364 |
| AdoMao | S-(5'-deoxy-5'-adenosyl)-1-aminoxy-4-(methylsulfonio)-2-cyclopentene | |
| APA | 1-Aminooxy-3-aminopropane | 65020 |
| AOE-PU | N-[2-aminooxyethyl]-1,4-diaminobutane | |
| AP-APA | 1-aminooxy-3-N-[3-aminopropyl]-aminopropane | |
| | 1,11-bis(ethyl)norspermine | |
| BES | 1,8-bis(ethyl)spermidine | |
| BES | 1,12-bis(ethyl)spermine | |
| DESPM | N1,N12-diethylspermine | |
| BE-3-3-3 | 1,11-bis(ethylamino)-4,8-diazaundecan | |
| BE-4-4-4 | 1,14-bis(ethylamino)-5,10-diazatetradecane | |
| DEHOP or DEHSPM | Diethylhomospermine, N1,N14-diethylhomospermine | |
| DENOP | diethyl-norspermine | |
| BE-4-4-4-4 | 1,19-bis(ethylamino)-5,10,15-triaza-nonadecane | |
| SL11037 | N-ethyl-N'-(2-(3'-ethylamino-propylamino methyl)-cis-cyclopropylmethyl)-propane 1,3-diamine tetrahydrochloride | |
| SL11038 | N-ethyl-N'-(2-(3'-ethylamino-propylamino methyl)-trans-cyclobutylmethyl)-propane 1,3-diamine tetrahydrochloride | |
| SL11044 | N-ethyl-N'-(2-(3'-ethylamino-propylamino methyl)-transcyclopropylmethyl)-propane 1,3-diamine tetrahydrochloride | |
| SL11047 or SL47 | N,N'-bis(3-ethylaminopropyl)-cis-but-2-ene-1,4-diaminetetrahydrochloride | |
| SL11093 or SL93 | N,N'-(cyclopropane-1,2-diylbis(methylene))bis(N4-ethylbutane-1,4-diamine) | |
| SL11090 | N1,N1'-(1R,2S)-cyclobutane-1,2-diylbis(methylene)bis(N3-methylpropane-1,3-diamine) | |
| SL11094 | N1,N1'-(1,2-phenylenebis(methylene))bis(N3-ethylpropane-1,3-diamine) | |
| SL11098 | N1,N1'-(cyclopropane-1,2-diylbis(methylene))bis(N4-ethylbutane-1,4-diamine) | |
| SL11099 | N1,N1'-(cyclobutane-1,2-diylbis(methylene))bis(N4-ethylbutane-1,4-diamine) | |
| SL11100 | N1,N1'-(cyclobutane-1,2-diylbis(methylene))bis(N4-ethylbutane-1,4-diamine) | |
| SL111105 | N1,N1'-(cyclopentane-1,2-diylbis(methylene))bis(N3-ethylpropane-1,3-diamine) | |

In further embodiments, the agent is a compound chosen from MGBG,

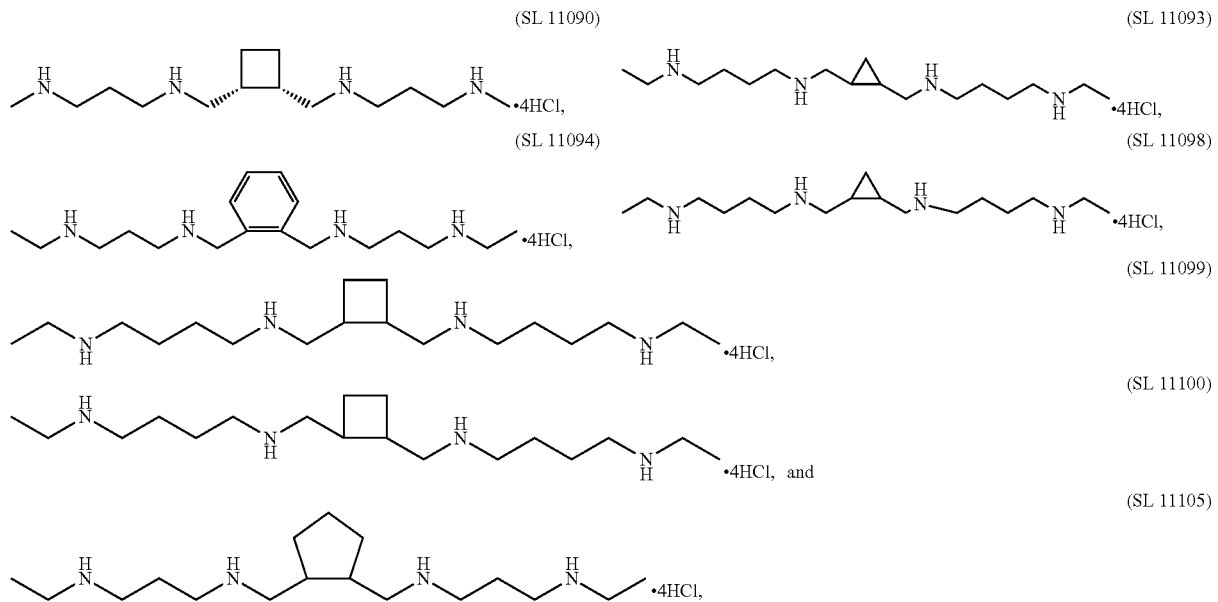

or a combination of two or more thereof. The two or more agents can be used either sequentially or simultaneously.

In further embodiments, the agent is a compound chosen from MGBG, MDL73811, CGP48664, Berenil, Pentamidine, SL47, and SL93, or a combination of two or more thereof. In yet further embodiment, the agent is MGBG, SL47 or SL93. The two or more agents can be used either sequentially or simultaneously.

MGBG

In certain embodiments, the compound is MGBG. MGBG is 1,1'[methylethanediylidene]dinitrilodiguanidine and is also known as methylglyoxal bis(guanylhydrazone), methyl-GAG, Me-G, and mitoguazone. As used herein, MGBG includes the free base and salts thereof. It is commonly, but not necessarily, used as a dihydrochloride salt/monohydrate. MGBG may be present as any one of the following isomers, or a tautomer and/or a syn/anti isomer thereof, mixture of one or more thereof:

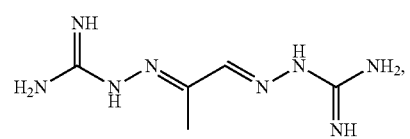

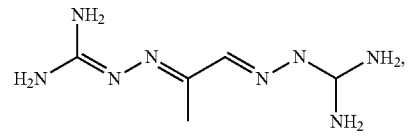

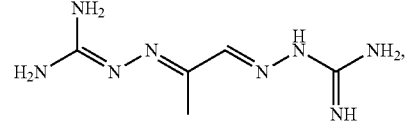

-continued

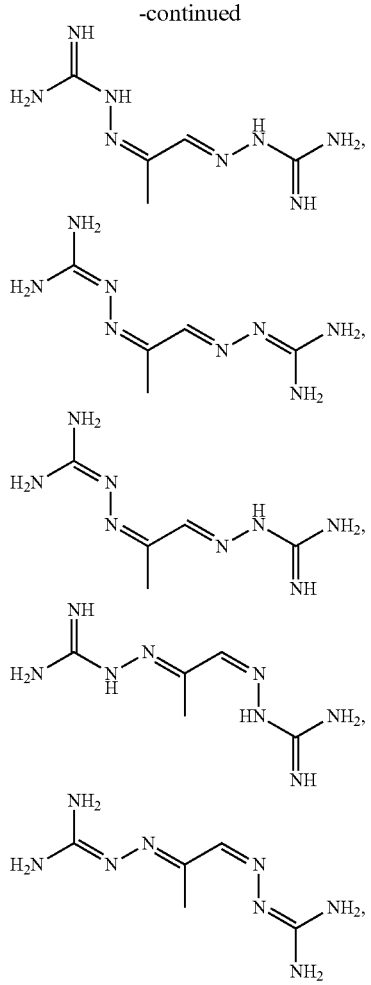

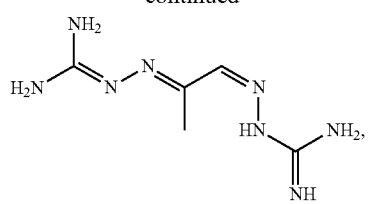

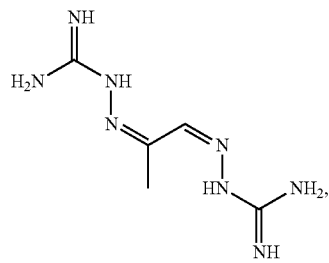

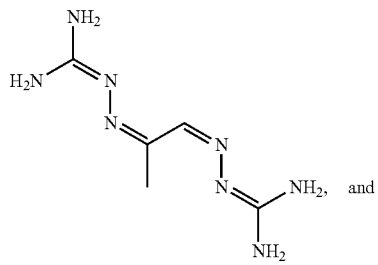

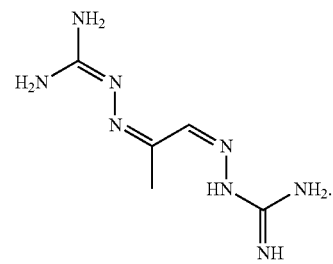

In certain embodiments, MGBG may be present as one of the following isomers, or a tautomer and/or a syn/anti isomer thereof, mixture of one or more thereof:

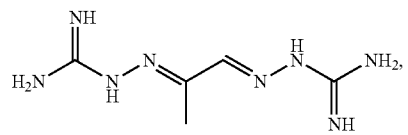

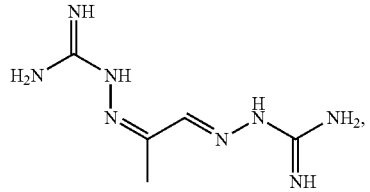

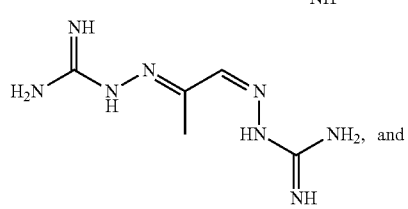

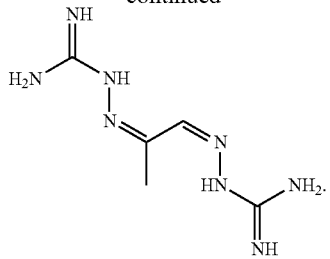

In certain embodiments, MGBG is used as the dihydrochloride salt of MGBG.

Additional polyamine analogs, polyamine biosynthesis inhibitors including SAMDC inhibitors, and other compounds useful in the embodiments of the invention disclosed herein are set forth in paragraphs [0086]-[0188] in U.S. patent application Ser. No. 12/837,753, filed Jul. 16, 2010, now issued as U.S. Pat. No. 8,258,186, the disclosures of which are incorporated by reference as if written herein in their entireties.

Pharmaceutical Compositions

The following are examples of dosage forms which may be used to orally deliver compounds disclosed herein.

Enterically Coated Capsules for Delayed Release

MGBG was encapsulated neat (undiluted) using Torpac gelatin capsules. Methylglyoxal bis (guanylhydrazone) dihydrochloride hydrate (MGBG), was used; a correction factor of 1.49 (to account for the dihydrochloride salt/monohydrate) was used when calculating the required amount of test article. The amount in each capsule was 10, 30, or 100 mg/kg, calculated based on subject body weight. Capsules were enterically coated with Eudragit® L100-55, as required, using a Torpac Pro-Coater® according to the standard dip procedure provided by the manufacturer (see www.torpac.com, go to "Reference/ProCoater Manual.pdf" or contact Torpac, Inc. for detailed instructions).

Immediate-Release Dosage Forms

Solid MGBG or a salt thereof may be passed through one or more sieve screens to produce a consistent particle size. Excipients, too, may be passed through a sieve. Appropriate weights of compounds, sufficient to achieve the target dosage per capsule, may be measured and added to a mixing container or apparatus, and the blend is then mixed until uniform. Blend uniformity testing may be done by, for example, sampling 3 points within the container (top, middle, and bottom) and testing each sample for potency. A test result of 95-105% of target, with an RSD of 5%, would be considered ideal; optionally, additional blend time may be allowed to achieve a uniform blend. Upon acceptable blend uniformity results, a measured aliquot of this stock formulation may be separated to manufacture the lower strengths. Magnesium stearate may be passed through a sieve, collected, weighed, added to the blender as a lubricant, and mixed until dispersed. The final blend is weighed and reconciled. Capsules may then be opened and blended materials flood fed into the body of the capsules using a spatula. Capsules in trays may be tamped to settle the blend in each capsule to assure uniform target fill weight, then sealed by combining the filled bodies with the caps.

300 mg Capsule: Total fill weight of capsule is 500 mg, not including capsule weight. Target compound dosage is 300 mg per capsule, but may be adjusted to account for the weight of counterions and/or solvates if given as a salt or solvated polymorph thereof. In such a case the weight of the other excipients, typically the filler, is reduced.

| Ingredient | Quantity per Capsule, mg |
|---|---|
| MGBG | 300.00 |
| Lactose monohydrate | 179.00 |
| Silicon dioxide | 3.00 |
| Crospovidone | 15.00 |
| Magnesium stearate (vegetable grade) | 3.00 |

150 mg Capsule: Total fill weight of capsule is 300 mg, not including capsule weight. Target compound dosage is 150 mg per capsule, but may be adjusted to account for the weight of counterions and/or solvates if given as a salt or solvated polymorph thereof. In such a case the weight of the other excipients, typically the filler, is reduced.

| Ingredient | Quantity per Capsule, mg |
|---|---|
| MGBG | 150 |
| Microcrystalline cellulose (MCC) | 147 |
| Magnesium stearate (vegetable grade) | 3 |

Compounds may additionally be formulated for oral delivery for immediate, delayed, or extended release. For example, compounds may be formulated as set forth in U.S. patent application Ser. No. 13/354,076, filed Jan. 19, 2012, the disclosure of which is incorporated by reference as if written herein in its entirety.

In Vitro Assays

MGBG was assayed for activity against 137 enzymes (including SAMDC, cyclooxygenase 1 (COX1), and COX2), receptors, ion channels, and transporters using methods previously described in the literature. MGBG is a nanomolar inhibitor of SAMDC (Ki=78 nM), which functionally inactivates monocytes/macrophages (reducing PGE2 and 8-isoprostane), without any effect on COX1 or COX2.

In Vivo Assays

MGBG anti-inflammatory and analgesic activities were studied in rodents using models well-known to those of skill in the art.

Pharmacokinetic Assays

PK was assessed in a series of IV/PO bioavailability studies in mice, rats, dogs, and non-human primates using LC/MS/MS-based methods. Animal data were scaled allometrically to predict the corresponding properties and doses in humans. Oral MGBG has a favorable PK profile in mice, rats, dogs, and non-human primates, suggesting considerable oral bioavailability (35%) and half-life (23 hours) in humans. Additional details are set forth in U.S. patent application Ser. No. 12/837,753, filed Jul. 16, 2010, now issued as U.S. Pat. No. 8,258,186 (for example in paragraphs [0308]-[0348]), the disclosures of which are incorporated by reference as if written herein in their entireties.

Carrageenan Air Pouch Model

For carrageenan air pouch, male Lewis rats (n=6/group) were dosed orally with vehicle and MGBG at doses from 1-60 mg/kg/day for 6 days, along with additional groups dosed orally with 10 mg/kg naproxen and 1 mg/kg dexamethasone one day prior to carrageenan injection. Air pouches were formed on the dorsum of rats during the last 4 days of drug dosing by injection of 20 mL of sterile air subcutaneously, with re-inflation one day prior to carrageenan injection. Carrageenan-stimulated prostaglandin E2 (PGE2) was determined by ELISA of pouch fluid at 3 and 24 hours.

In rodent air pouches, the drug inhibits carrageenan-stimulated peak inflammatory production (at 24 hours) of PGE2 by monocytes/macrophages while sparing basal levels (at 3 hours), in contrast to naproxen and dexamethasone which suppress PGE2 at both time-points.

Carrageenan Paw Edema and Hyperalgesia Model

In murine carrageenan-induced paw edema and hyperalgesia, male Swiss Webster mice (n=16/group) were dosed orally twice-daily with vehicle and MGBG doses ranging from 3-30 mg/kg for 3 days, along with an additional group dosed orally with 1 mg/kg dexamethasone 1 hour prior to injection of 1% carrageenan into the right hind paw. Paw edema and hyperalgesia were measured over 24 hours by plethysmometry and paw withdrawal latency to a thermal stimulus, respectively. In rat carrageenan-induced paw edema and hyperalgesia, male Sprague-Dawley rats (n=10/group) were dosed orally once-daily with vehicle, 60 mg/kg/day MGBG, 20 mg/kg/day celecoxib, and 30 mg/kg/day naproxen for 5 days. Additionally, 1 mg/kg dexamethasone was dosed the night before and 2 hours prior to carrageenan injection into the right hind paw. Paw edema and hyperalgesia were measured over 6 hours by plethysmometry and withdrawal latency to a thermal stimulus, respectively.

MGBG efficacy in carrageenan-induced paw edema and hyperalgesia is comparable to that of celecoxib, and preliminary dose-ranging studies suggest considerable activity at dose levels as low as 3 mg/kg/day in rats.

Collagen-Induced Arthritis Model

For murine collagen-induced arthritis, male DBA/1 mice (n=15/group) were immunized intradermally with bovine type II collagen in the presence of complete Freund's adjuvant on two occasions (separated by 3 weeks), and dosed concurrently with twice-daily oral administrations of vehicle, 30 mg/kg MGBG, and 0.2 mg/kg dexamethasone for 34 days. Mouse paw joints were scored for arthritis based upon scales previously described in the literature. Although MGBG is anti-inflammatory, the drug does not have disease-modifying anti-rheumatic (DMARD) activity in collagen-induced arthritis (model of rheumatoid arthritis), as it only ameliorates the early signs of inflammation in arthritic paws (e.g., swelling).

Figure 2:
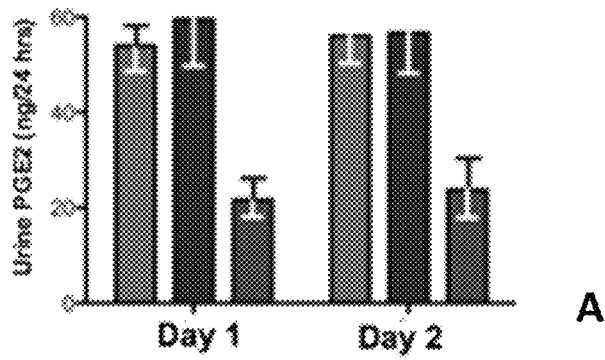
FIG. 2 shows the effect of high-dose oral MGBG, compared to naproxen and vehicle (placebo), on urine PGE2 (A), sodium (B), and isoprostane-8 (C). In each graph, placebo is represented by the bar to the left, MGBG in the center, and naproxen to the right.
Figure 2:
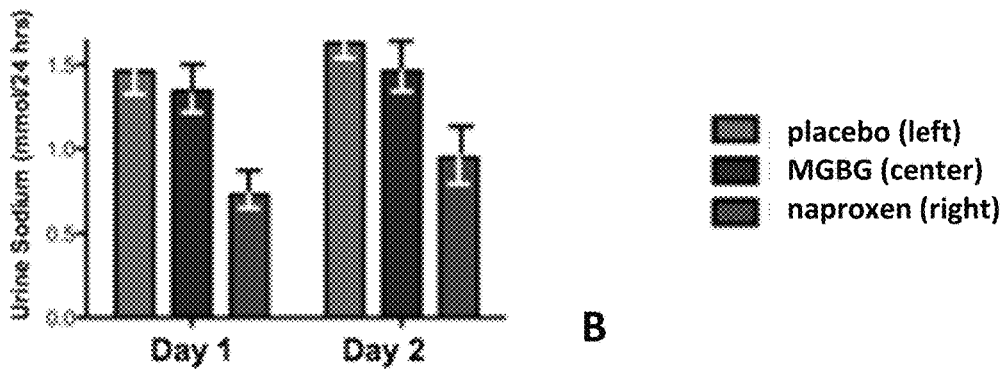
Figure 2:
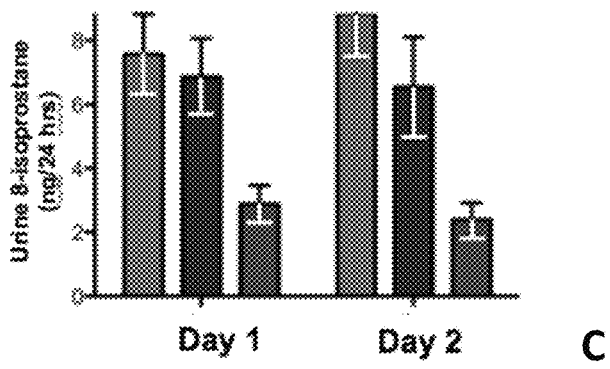

Renal Physiology Model:

Renal physiology studies were conducted in male Sprague-Dawley rats (n=8/group) housed in metabolic cages. Rats were orally dosed with vehicle, 30 mg/kg MGBG (Qday), or 20 mg/kg naproxen (TID) for two days, during which urine was collected. Urine electrolytes and creatinine were measured using a clinical chemistry analyzer by AVL (St. Louis, Mo.), as well as PGE2 and 8-isoprostane by ELISA. In contrast to naproxen, MGBG has no effect on rat renal-derived PGE2 or natriuresis (COX2-dependent process), or 8-isoprostane production. See also FIG. 2.

Rat Platelet Aggregation Studies:

Platelet aggregation was measured by absorbance of collagen-stimulated platelet rich plasma isolated from Sprague-Dawley rats (n=4/group) orally dosed for 5 days with vehicle, 60 mg/kg MGBG, 30 mg/kg naproxen, and 20 mg/kg celecoxib. MGBG has no effect on platelet aggregation. See also FIG. 1.

Human Platelet Aggregation Studies:

The purpose of this study was to compare the effects of MGBG on human platelet aggregation to those of marketed anti-inflammatory drugs: naproxen, celecoxib, and aspirin.

Human, unconcentrated platelet rich plasma (PRP, Interstate Blood Bank, Memphis, Tenn.), was obtained in one-unit volumes (~200-300 mL) from three human donors, from which whole blood had been collected into an anticoagulant (ACD-type A). Units were received within 24 hrs of collection and at steady ambient temperatures (~20° C.). Actual platelet counts were provided by the supplier and were all found to be within the normal human physiologic range.

PRP was divided into aliquots of ~45 mL each in 50-mL centrifuge tubes. The centrifuge tubes were then subjected to a 15-min spin (~1100 rpm) in a Beckman model GPR centrifuge with a GH 3.7 swinging bucket rotor, in order to pellet out any cellular contamination. Following centrifugation, the top 40 mL was harvested and allowed to "rest" at room temperature before proceeding with the experiment.

Before pipetting, the tube containing the clarified PRP was gently inverted 3-4 times, and 190 μL of PRP was pipetted into the wells of a Costar 96-well flat bottom microtiter plate (#3595). A 5-μL volume of test compound and positive controls (aspirin and naproxen) were added (in triplicate) to the wells. The microplate was then inserted into the microplate reader (Molecular Devices model 340PC384) where it was allowed to equilibrate for 10 minutes with intermittent shaking at 37° C. At the end of the equilibration period, arachidonic acid (Nu-Chek Prep, Inc) was added in a volume of 5 μL. The final concentration of arachidonic acid in the well was 0.5 mM. A minimum of 3 (and up to 12) wells of the plate had only 5 μL of vehicle added to them (no compounds). These wells either had 5 μL of PBS (0% aggregation) or 5 μL of agonist (100% aggregation), and were used to generate a standard curve. The plate was then read using "kinetic read" mode for a period of 15 minutes, taking readings every 15 seconds (wavelength=632 nm) with agitation in between each reading. The area under the curve (AUC) was generated from data for each well using the instrument software (SoftMax Pro ver. 5.0.1).

Results are shown below in the following tables, where the mean and error (standard deviation) are calculated for replicate measurements within each donor. Where the value is marked with an asterisk, it is the average of two replicates; otherwise, it is the average of at least three. These data demonstrate that neither MGBG nor celecoxib inhibit platelet aggregation. In comparison, naproxen and aspirin inhibited platelet aggregation.

| | Compound Dose | Vehicle (no arachidonic acid) N/A | Vehicle (arachidonic acid) 0.5 mM | ASA 30 μM | 100 μM | 0.5 mM | 1 mM |
|---|---|---|---|---|---|---|---|
| Donor 1 | Mean AUC | 353.4 | 107.3 | 112.1* | 108.7* | 137.6 | 276.2 |
| | Error | 6 | 19.7 | 8.6* | 11.5* | 5.2 | 11.5 |
| Donor 2 | Mean AUC | 346.4 | 112.7 | 138 | 131.5 | 178.9 | 246.1 |
| | Error | 8.4 | 17.9 | 22.6 | 3.5 | 10.6 | 1.9 |
| Donor 3 | Mean AUC | 334.9 | 118.1 | 129.8 | 121.7 | 160.5 | 225.2 |
| | Error | 3.6 | 11.9 | 15.3 | 17 | 15.2 | 3.3 |

| | Compound Dose | Vehicle (no arachidonic acid) N/A | Vehicle (arachidonic acid) 0.5 mM | Celecoxib 0.1 μM | 0.3 μM | 1 μM | 3 μM |
|---|---|---|---|---|---|---|---|
| Donor 1 | Mean AUC | 353.4 | 107.3 | 101.6 | 93.7 | 110.8 | 93.8 |
| | Error | 6 | 19.7 | 8.9 | 10.4 | 20.3 | 7.7 |
| Donor 2 | Mean AUC | 346.4 | 112.7 | 125 | 131.4* | 127.7 | 130.9 |
| | Error | 8.4 | 17.9 | 6 | 29.6* | 10.7 | 6.2 |
| Donor 3 | Mean AUC | 334.9 | 118.1 | 111 | 130.8 | 113.2 | 122.4 |
| | Error | 3.6 | 11.9 | 8.1 | 11 | 6.8 | 8 |

| | Compound Dose | Vehicle (no arachidonic acid) N/A | Vehicle (arachidonic acid) 0.5 mM | MGBG 0.1 μM | 0.3 μM | 1 μM | 3 μM |
|---|---|---|---|---|---|---|---|
| Donor 1 | Mean AUC | 353.4 | 107.3 | 104.1 | 102.2 | 91.4 | 94.5 |
| | Error | 6 | 19.7 | 7 | 16.4 | 3.4 | 2.8 |
| Donor 2 | Mean AUC | 346.4 | 112.7 | 110.8 | 121.9 | 129.8 | 123.5 |
| | Error | 8.4 | 17.9 | 7.5 | 15.2 | 7.1 | 7.2 |
| Donor 3 | Mean AUC | 334.9 | 118.1 | 114.3* | 122.8 | 126.2* | 128.6 |
| | Error | 3.6 | 11.9 | 3.1* | 18.5 | 3.6* | 19.7 |

|  |  | Vehicle (no arachidonic acid) | Vehicle (arachidonic acid) | Naproxen | | | |
|---|---|---|---|---|---|---|---|
|  | Compound Dose | N/A | 0.5 mM | 1 μM | 3 μM | 10 μM | 30 μM |
| Donor 1 | Mean AUC | 353.4 | 107.3 | 114 | 106.9 | 148.8 | 304.3 |
| | Error | 6 | 19.7 | 30.8 | 10.2 | 6.5 | 3.2 |
| Donor 2 | Mean AUC | 346.4 | 112.7 | 126.5 | 132.4 | 307 | 322.8 |
| | Error | 8.4 | 17.9 | 13.5 | 4.6 | 5.4 | 4.9 |
| Donor 3 | Mean AUC | 334.9 | 118.1 | 131.8 | 138.6 | 143.8 | 183.8 |
| | Error | 3.6 | 11.9 | 18.7 | 13.4 | 13.7 | 7.9 |

Toxicology Studies

Gastrointestinal (GI) tract mucosa was assessed in the context of a full battery of toxicology and safety studies. MGBG spares the GI tract at considerable multiples of the efficacious dose. Fourteen-day toxicology studies have demonstrated greater than 20- and 189-fold safety margins in rats and minipigs, respectively. See, e.g., U.S. patent application Ser. No. 13/354,076, filed Jan. 19, 2012, the disclosure of which is incorporated by reference as if written herein in its entirety.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of treatment of pain or inflammation in an elderly patient in need thereof, comprising administering a therapeutically effective amount of methylglyoxal bis(guanylhydrazone) (MGBG), wherein the therapeutically effective amount of MGBG does not inhibit cyclooxygenase and is not an opioid or a steroid, and is gastrointestinal-, platelet-, and renal-sparing.

2. The method as recited in claim 1, wherein the patient is over 50 years of age.

3. The method as recited in claim 1, wherein the patient is over 60 years of age.

4. The method as recited in claim 1, wherein the patient is over 65 years of age.

5. The method as recited in claim 1, wherein the patient is over 70 years of age.

6. The method as recited in claim 1, wherein the compound is formulated for oral delivery.

7. The method as recited in claim 6, wherein the compound is formulated for delayed-release oral delivery to the small bowel.

8. The method as recited in claim 6, wherein NSAID drugs are contraindicated in the elderly patient.

9. The method as recited in claim 6, wherein the elderly patient has a bleeding or clotting disorder.

10. The method as recited in claim 6, wherein the elderly patient has an increased risk for bleeding.

11. The method as recited in claim 6, wherein the elderly patient has a gastrointestinal disorder.

12. The method as recited in claim 6, wherein the elderly patient has a renal disorder.

13. The method as recited in claim 6, wherein the elderly patient has a disorder in which sodium/fluid retention is undesirable.

14. The method as recited in claim 6, wherein the elderly patient is taking an anticoagulant drug.

15. The method as recited in claim 6, wherein the elderly patient has a renal disease, congestive heart failure, or cirrhosis, or is volume-depleted or dehydrated.

16. The method as recited in claim 6, wherein the elderly patient has cirrhosis or thrombocytopenia.

17. The method as recited in claim 6, wherein the elderly patient is pre-operative for surgery.

18. The method as recited in claim 6, wherein the elderly patient has a history of peptic ulcer disease or at increased risk of gastrointestinal bleeding/ulceration/obstruction.

* * * * *